US008029689B2

(12) United States Patent
Nishida et al.

(10) Patent No.: US 8,029,689 B2
(45) Date of Patent: Oct. 4, 2011

(54) METHOD FOR PRODUCING HIGH-PURITY QUATERNARY AMMONIUM SALT

(75) Inventors: Tetsuo Nishida, Izumiotsu (JP); Kazutaka Hirano, Izumiotsu (JP); Akinori Oka, Tokushima (JP); Yoshinobu Abe, Tokushima (JP); Akihiro Nabeshima, Tokushima (JP)

(73) Assignees: Otsuka Chemical Co., Ltd., Osaka (JP); Stella Chemifa Corporation, Osaka (JP)

( * ) Notice: Subject to any disclaimer, the term of this patent is extended or adjusted under 35 U.S.C. 154(b) by 310 days.

(21) Appl. No.: 12/311,067

(22) PCT Filed: Sep. 18, 2007

(86) PCT No.: PCT/JP2007/068596

§ 371 (c)(1), (2), (4) Date: Mar. 18, 2009

(87) PCT Pub. No.: WO2008/035796

PCT Pub. Date: Mar. 27, 2008

(65) Prior Publication Data

US 2010/0044617 A1 Feb. 25, 2010

(30) Foreign Application Priority Data

Sep. 19, 2006 (JP) ................................ 2006-252229

(51) Int. Cl.
*H01G 9/02* (2006.01)
*C07C 209/00* (2006.01)

(52) U.S. Cl. ...................................... 252/62.2; 564/296

(58) Field of Classification Search ................ 252/62.2, 252/625.2; 564/296
See application file for complete search history.

(56) References Cited

U.S. PATENT DOCUMENTS

2004/0130852 A1 7/2004 Matsumoto et al.

FOREIGN PATENT DOCUMENTS

| | | |
|---|---|---|
| GB | 1 052 339 | 12/1966 |
| JP | 57-171940 | 10/1982 |
| JP | 10-287630 | 10/1998 |
| JP | 2000-226360 | 8/2000 |
| JP | 2004-186246 | 7/2004 |
| JP | 2005-272311 | 10/2005 |
| JP | 2006-143647 | 6/2006 |
| JP | 2006-257039 | 9/2006 |

OTHER PUBLICATIONS

International Search Report issued Dec. 25, 2007 in the International (PCT) Application of which the present application is the U.S. National Stage.

Supplementary European Search Report issued Sep. 14, 2010 in European Application No. EP 07 82 8372.

Database WPI Week, 198248, Thomson Scientific, London, GB; AN 1982-03427J, XP002600480 & JP 57-171940, Oct. 22, 1982, Abstract.

Database WPI Week, 200569, Thomson Scientific, London, GB; AN 2005-670718, XP002600618 & JP 2005-272311,Oct. 6, 2005, Abstract.

*Primary Examiner* — Porfirio Nazario Gonzalez

(74) *Attorney, Agent, or Firm* — Wenderoth, Lind & Ponack, L.L.P.

(57) ABSTRACT

A process for preparing a high-purity quaternary ammonium salt comprising:

(1) adding an oxide or hydroxide of a Group 1, 2, 12 or 13 metal to a quaternary ammonium salt containing a protonic acid salt of a tertiary amine as an impurity and thereby neutralizing the tertiary amine protonic acid salt with the metal oxide or hydroxide to convert the acid salt to a tertiary amine and water and to convert the metal oxide or hydroxide to a metal salt at the same time, and (2) removing the tertiary amine, water and metal salt produced from the system.

7 Claims, No Drawings

METHOD FOR PRODUCING HIGH-PURITY QUATERNARY AMMONIUM SALT

This application is a U.S. national stage of International Application No. PCT/JP2007/068596 filed Sep. 18, 2007.

TECHNICAL FIELD

The present invention relates to a process for preparing quaternary ammonium salts for use as electrolytes in electric double layer capacitors, electrolytic capacitors and like capacitor elements by reducing the amounts of a tertiary amine and a tertiary amine protonic acid salt contained as impurities in quaternary ammonium salts.

BACKGROUND ART

For preparing quaternary ammonium salts, already known are a process comprising reacting an alkyl halide with a tertiary amine to obtain a quaternary ammonium halide and reacting an acid with the halide, and a process comprising reacting a carbonic acid diester with a tertiary amine to produce a quaternary ammonium salt and subsequently reacting an acid with the salt for decarbonation.

In the case where the tertiary amine is not completely converted to a quaternary compound in either of these processes, the tertiary amine left unreacted will react with the acid in the next step to produce a protonic acid salt of the tertiary amine, permitting the acid salt to remain in the main product of quaternary ammonium salt.

The quaternary ammonium halide or quaternary ammonium salt is likely to produce a tertiary amine when thermally decomposed. The tertiary amine produced provides a tertiary amine protonic acid salt in the process for preparing the quaternary ammonium salt. Since the hydrogen atom of the cation of the tertiary amine protonic acid salt is liable to become released as a proton, the acid salt is unstable to a reducing reaction, so that the acid salt is known to be responsible for the diminution of the voltage resistance and long-term reliability of electric double layer capacitors and electrolytic capacitors (for example, Patent Literature 1).

Accordingly, it is required to reduce the amounts of the tertiary amine and tertiary amine protonic acid salt which are present in quaternary ammonium salts for use as electrolytes in order to obtain highly reliable electric double layer capacitors and electrolytic capacitors.

In reducing the amounts of the tertiary amine and tertiary amine protonic acid salt in quaternary ammonium salts, it is known to recrystallize the salt in an organic solvent (Patent Literature 1, 2).

However, this method is not suitable to practice industrially, for example, because the crystallization leads to a lower yield. Furthermore, it is difficult to effect the recrystallization if the quaternary ammonium salt is a liquid substance at room temperature.

[Patent Literature 1] JP2000-311839A

[Patent Literature 2] JP2004-186246A

An object of the present invention is to provide a process for preparing quaternary ammonium salts by reducing the amounts of a tertiary amine and a tertiary amine protonic acid salt contained as impurities in quaternary ammonium salts.

DISCLOSURE OF THE INVENTION

The present invention provides the following.

1. A process for preparing a high-purity quaternary ammonium salt comprising:
 (1) adding an oxide or hydroxide of a Group 1, 2, 12 or 13 metal to a quaternary ammonium salt containing a protonic acid salt of a tertiary amine as an impurity and thereby neutralizing the tertiary amine protonic acid salt with the metal oxide or hydroxide to convert the acid salt to a tertiary amine and water and to convert the metal oxide or hydroxide to a metal salt at the same time, and
 (2) removing the tertiary amine, water and metal salt produced from the system.

2. A process for preparing a high-purity quaternary ammonium salt comprising:
 (1) reacting a tertiary amine with an alkyl halide having or not having a substituent to obtain a quaternary ammonium halide salt,
 (2) reacting an acid compound with the halide salt to obtain a quaternary ammonium salt containing a tertiary amine protonic acid salt as an impurity,
 (3) adding an oxide or hydroxide of a Group 1, 2, 12 or 13 metal to the quaternary ammonium salt and thereby neutralizing the tertiary amine protonic acid salt with the metal oxide or hydroxide to convert the acid salt to a tertiary amine and water and to convert the metal oxide or hydroxide to a metal salt at the same time, and
 (4) removing the tertiary amine, water and metal salt produced from the system.

According to the invention, the term a protonic acid salt of a tertiary amine refers to a tertiary amine salt having releasable $H^+$ in the molecule.

The present invention provides a process for preparing a high-purity quaternary ammonium salt which process comprises: (1) adding an oxide or hydroxide of a Group 1, 2, 12 or 13 metal to a quaternary ammonium salt containing a protonic acid salt of a tertiary amine as an impurity and thereby neutralizing the tertiary amine protonic acid salt with the metal oxide or hydroxide to convert the acid salt to a tertiary amine and water and to convert the metal oxide or hydroxide to a metal salt at the same time, and (2) removing the tertiary amine, water and metal salt produced from the system.

Examples of quaternary ammonium cations of the quaternary ammonium salts used in the invention can be tetraalkylammonium, tetraalkylphosphonium, imidazolium, pyrazolium, pyridinium, triazolium, pyridazinium, thiazolium, oxazolium, pyrimidinium, pyrazinium, etc.

The following compounds are specifically exemplified.

As tetraalkylammonium are tetraethylammonium, tetramethylammonium, tetrapropylammonium, tetrabutylammonium, triethylmethylammonium, trimethylethylammonium, dimethyldiethylammonium, trimethylpropylammonium, trimethylbutylammonium, dimethylethylpropylammonium, methylethylpropylbutylammonium, N,N-dimethylpyrrolidinium, N-ethyl-N-methylpyrrolidinium, N-methyl-N-propylpyrrolidinium, N-ethyl-N-propylpyrrolidinium, N,N-dimethylpiperidinium, N-methyl-N-ethylpiperidinium, N-methyl-N-propylpiperidinium, N-ethyl-N-propylpiperidinium, N,N-dimethylmorpholinium, N-methyl-N-ethylmorpholinium, N-methyl-N-propylmorpholinium, N-ethyl-N-propylmorpholinium, trimethylmethoxyammonium, dimethylethylmethoxymethylammonium, dimethylpropylmethoxymethylammonium, dimethylbutylmethoxymethylammonium, diethylmethymethoxymethylammonium, methylethylpropylmethoxymethylammonium, triethylmethoxymethylammonium, diethylpropylmethoxymethylammonium, diethylbutylmethoxymethylammonium, dipropylmethylmethoxymethylammonium, dipropylethylmethoxymethylammonium, tripropylmethoxymethylammonium, tributylmethoxymethylammonium, trimethylethoxymethylammonium, dimethylethylethoxymethylammonium, dimethylpropylethoxymethylammonium, dimethylbutylethoxymethylammonium, diethylmethylethoxymethylammonium, triethylethoxymethylammonium, diethylpropylethoxymethylammonium, diethylbutylethoxymethylammonium, dipropylmethylethoxymethylammonium, dipropylethylethoxymethylammonium, tripropylethoxymethylammonium, tributylethoxymethylammonium, N-methyl-N-methoxymethylpyrrolidinium, N-ethyl-N-methoxymethylpyrrolidinium, N-propyl-N-methoxymethylpyrrolidinium, N-butyl-N-methoxymethylpyrrolidinium, N-methyl-N-ethoxymethylpyrrolidinium, N-methyl-N-propoxymethylpyrrolidinium, N-methyl-N-butoxymethylpyrrolidinium, N-methyl-N-methoxymethylpiperidinium, N-ethyl-N-methoxymethylpyrrolidinium, N-methyl-N-ethoxymethylpyrrolidinium, N-propyl-N-methoxymethylpyrrolidinium, N-methyl-N-propoxymethylpyrrolidinium, 4-azoniaspiro[3,4]octane, 3-azoniaspiro[2,4]heptane, 5-azoniaspiro[5,5]undecane, etc.

As tetraalkylphosphonium are tetraethylphosphonium, tetramethylphosphonium, tetrapropylphosphonium, tetrabutylphosphonium, triethylmethylphosphonium, trimethylethylphosphonium, dimethyldiethylphosphonium, trimethylpropylphosphonium, trimethylbutylphosphonium, dimethylethylpropylphosphonium, methylethylpropylbutylphosphonium, etc.

As imidazolium are 1,3-dimethylimidazolium, 1-ethyl-3-methylimidazolium, 1,3-diethylimidazolium, 1,2-dimethyl-3-ethylimidazolium, 1,2-dimethyl-3-propylimidazolium, etc.

As pyrazolium are 1,2-dimethylpyrazolium, 1-methyl-2-ethylpyrazolium, 1-propyl-2-methypyrazolium, 1-methyl-2-butylpyrazolium, etc.

As pyridinium are N-methylpyridinium, N-ethylpyridinium, N-propylpyridinium, N-butylpyridinium, etc.

As triazolium are 1-methyltriazolium, 1-ethyltriazolium, 1-propyltriazolium, 1-butyltriazolium, etc.

As pyridazinium are 1-methylpyridazinium, 1-ethylpyridazinium, 1-propylpyridazinium, 1-butylpyridazinium, etc.

As thiazolium are 1,2-dimethylthiazolium, 1,2-dimethyl-3-propylthiazolium, etc.

As oxazolium are 1-ethyl-2-methyloxazolium, 1,3-dimethyloxazolium, etc.

As pyrimidinium are 1,2-dimethylpyrimidinium, 1-methyl-3-propylpyrimidinium, etc.

As pyrazinium are 1-ethyl-2-methylpyrazinium, 1-butylpyrazinium, etc.

Examples of anions of quaternary ammonium salts usable in the present invention are $CF_3CO_2^-$, $CF_3SO_3^-$, $BF_4^-$, $AlF_4^-$, $ClBF_3^-$, $(FSO_2)_2N^-$, $PF_6^-$, $AsF_6^-$, $ClO_4^-$, $N(CF_3SO_3)_2^-$, $C(CF_3SO_3)_3^-$, $RfSO_3^-$, $RfCO_2^-$ (Rf is fluoroalkyl having 1 to 8 carbon atoms), $(R^{r1}SO_2)(R^{r2}SO_2)N^-$ and $(R^{r1}SO_2)(R^{r2}CO_2)^-$ ($R^{r1}$ and $R^{r2}$ are the same or different and are each fluoroalkyl having 1 to 8 carbon atoms). Preferable are $CF_3CO_2^-$, $CF_3SO_3^-$, $BF_4^-$, $AlF_4^-$, $ClBF_3^-$ or $(FSO_2)_2N^-$.

Examples of metal hydroxides or metal oxides usable in the present invention are $Ca(OH)_2$, $Mg(OH)_2$, $Ba(OH)_2$, $Zn(OH)_2$, $Al(OH)_3$, CaO, MgO, BaO, ZnO, $Al_2O_3$ and LiOH. These are usable singly or in a mixture of at least two of them.

Examples of the mixture are $Ba(OH)_2$ and BaO, $Ba(OH)_2$ and MgO, $Ca(OH)_2$ and CaO, $Mg(OH)_2$ and BaO, $Al(OH)_3$ and CaO, etc. Preferable metal hydroxides are $Ca(OH)_2$, $Mg(OH)_2$, $Ba(OH)_2$ and $Al(OH)_3$. Preferable metal oxides are CaO, MgO, BaO, ZnO and $Al_2O_3$.

Tertiary amine protonic acid salts which are impurities according to the present invention are produced when quaternary ammonium salts are produced. The acid salt is produced also when the quaternary ammonium salt is thermally decomposed. For example, in preparing $BF_4$ salt of N-methoxymethyl-N-methylpyrrolidinium, hydrochloric acid present as an impurity in chloromethyl methyl ether serving as a material reacts with methylpyrrolidine, a tertiary amine serving as another material, to produce hydrochloride of methylpyrrolidine. Alternatively, chloromethyl methyl ether is hydrolyzed with a very small amount of water present in methylpyrrolidine or in a solvent to produce hydrochloric acid, permitting this acid to form hydrochloride of methylpyrrolidine through the same reaction as above. Through a salt conversion reaction wherein $HBF_4$ is used, this hydrochloride is made into $HBF_4$ salt of methylopyrrolidine which is very difficult to remove. Further when the $BF_4$ salt is prepared at a high temperature of 130 to 200° C., the thermal decomposition of N-methoxymethyl-N-methylpyrrolidinium salts (hydrochloride, $BF_4$ salt) produces methylpyrrolidine $HBF_4$ salt although in a small amount. Further when an excess of methylpyrrolidine is used, methylpyrrolidine remains in N-methoxymethyl-N-methylpyrrolidinium hydrochloride, and the subsequent conversion to $BF_4$ salt produces N-methylpyrrolidinium $HBF_4$ salt.

As the tertiary amines, the following compounds are specifically exemplified.

Triethylamine, trimethylamine, tripropylamine, tributylamine, dimethylethylamine, dimethylpropylamine, dimethylbutylamine, diethylmethylamine, diethylpropylamine, diethylbutylamine, dipropylbutylamine, dibutylpropylamine, methylethylpropylamine, methylethylbutylamine, ethylpropylbutylamine, N-methylpyrrolidine, N-ethylpyrrolidine, N-propylpyrrolidine, N-butylpyrrolidine, N-methylpiperidine, N-ethylpiperidine, N-propylpiperidine, N-butylpiperidine, N-methylmorpholine, N-ethylmorpholine, N-propylmorpholine, N-butylmorpholine, dimethylmethoxymethylamine, diethylmethoxymethylamine, dipropylmethoxymethylamine, dibutylmethoxymethylamine, ethylmethylmethoxymethylamine, methylpropylmethoxymethylamine, methylbutylmethoxymethylamine, ethylpropylmethoxymethylamine, ethylbutylmethoxymethylamine, propylbutylmethoxymethylamine, dimethylethoxymethylamine, diethylethoxymethylamine, dipropylethoxymethylamine, dibutylethoxymethylamine, ethylmethylethoxymethylamine, methylpropylethoxymethylamine, ethylpropylethoxymethylamine, ethylbutylethoxymethylamine, propylbutylethoxymethylamine, N-methoxymethylpyrrolidine, N-ethoxymethylpyrrolidine, N-propoxymethylpyrrolidine, N-butoxymethylpyrrolidine, N-ethoxymethylpyrrolidine, N-propoxymethylpyrrolidine, etc.

Examples of imidazoles are 1-methylimidazole, 1-ethylimidazole, 1,2-dimethylimidazole, 1-methyl-2-ethylimidazole, etc.

Examples of pyrazoliums are 1-methylpyrazole, 1-ethylpyrazole, 1-propylpyrazole, 3-methylpyrazole, etc. Also exemplified are pyridine, triazole, pyridazine, pyrazine, 1-methylthiazole, 1-methyloxazole, etc.

Further, examples of protonic acid salts of the tertiary amines are protonic acid salts of the above tertiary amines, the protonic acids being $CF_3CO_2H$, $CF_3SO_3H$, $HBF_4$, $HAlF_4$, $HClBF_3$, $(FSO_2)_2NH$, $HPF_6$, $HAsF_6$, $HClO_4$, $NH(CF_3SO_3)_2$, $HC(CF_3SO_2)_3$, $RfSO_3H$, $RfCO_2H$ (Rf is fluoroalkyl having 1 to 8 carbon atoms), $(R^{r1}SO_2)$ $(R^{r2}SO_2)NH$ and $(R^{r1}SO_2)$ $(R^{r2}CO_2)H$ ($R^{r1}$ and $R^{r2}$ are the same or different and are each fluoroalkyl having 1 to 8 carbon atoms).

A description will be given of the process of the invention for preparing a high-quality quaternary ammonium salt.

A tertiary amine serving as the starting material is reacted with an alkyl halide which may have a substituent to thereby produce a quaternary ammonium halide salt. The quaternary ammonium halide salt is then reacted with an acid compound to prepare a quaternary ammonium salt.

Examples of acid compounds are $CF_3CO_2H$, $CF_3SO_3H$, $HBF_4$, $HAlF_4$, $HClBF_3$, $(FSO_2)_2NH$, $HPF_6$, $HAsF_6$, $HClO_4$, $NH(CF_3SO_3)_2$, $CH(CF_3SO_3)_3$, $RfSO_3H$, $RfCO_2H$ (Rf is fluoroalkyl having 1 to 8 carbon atoms), $(R^{r1}SO_2)$ $(R^{r2}SO_2)NH$ and $(R^{r1}SO_2)$ $(R^{r2}CO_2)H$ ($R^{r1}$ and $R^{r2}$ are the same or different and are each fluoroalkyl having 1 to 8 carbon atoms). Preferable are $CF_3CO_2H$, $CF_3SO_3H$, $HBF_4$, $HAlF_4$, $HClBF_3$ or $(FSO_2)_2NH$.

The quaternary ammonium salt obtained contains as an impurity a very small amount of a tertiary amine protonic acid salt resulting from the starting material of tertiary amine.

Subsequently, an oxide or hydroxide of a Group 1 2, 12 or 13 metal is added for reaction (neutralization) to the quaternary ammonium salt containing the impurity. The oxide or hydroxide of Group 1, 2, 12 or 13 metal is added in an amount of 0.5 to 2000 equivalents, preferably 1 to 1000 equivalents, based on the mole number of the tertiary amine protonic acid salt. An enhanced effect is available by using an increased amount of the metal oxide or hydroxide or the oxide or hydroxide having reduced particle sizes, i.e., increased surface areas.

The addition is made at a temperature of −20° C. to 200° C., preferably 10° C. to 150° C., more preferably 25° C. to 130° C. The reaction time is 10 minutes to 20 hours, preferably 30 minutes to 10 hours.

The reaction converts the oxide or hydroxide of Group 1, 2, 12 or 13 metal to a metal salt, and the tertiary amine protonic acid salt to a tertiary amine and water. For example when calcium oxide, magnesium oxide, barium oxide or the like is used, the metal salt is converted to the calcium, magnesium or barium salt of the anion. For example, in the case of tetrafluoroboric acid salt, the metal salt is converted to calcium tetrafluoroborate, magnesium tetrafluoroborate or barium tetrafluoroborate. The salt also reacts with the water produced and is converted to calcium hydroxide, magnesium hydroxide or barium hydroxide, whereby the amount of water can be diminished. The metal salt is removable, for example, by filtration or column purification.

The tertiary amine and water can be distilled off by a usual method, for example, by distillation in a vacuum or by heating, or by the combination of these methods. They are removable also by heating while introducing nitrogen, argon or air that will not react with the quaternary ammonium salt.

The tertiary amine and water are distilled off at a temperature of 20° C. to 200° C., preferably 90° C. to 170° C. for 0.5 to 24 hours, preferably 5 to 18 hours.

The quaternary ammonium salt resulting from the removal of impurities is reduced in the amounts of impurities, i.e., tertiary amine and tertiary amine protonic acid salt.

The high-purity quaternary ammonium salt prepared according to the present invention is favorably usable as an electrolyte or electrolytic solution, for example, in electric double layer capacitors, electrolytic capacitors and cells.

The smaller the content of the tertiary amine protonic acid salt in the electrolyte required of electrolytes for nonaqueous electrolysis, the better from the viewpoint of a reduction in the voltage resistance of electric double layer capacitors, electrolytic capacitors or cells and the diminution of the reliability thereof. The impurity content is up to 200 ppm, preferably up to 100 ppm, more preferably 50 ppm, most preferably up to 30 ppm, especially up to 10 ppm.

The concentration of the tertiary amine protonic acid salt can be determined by liquid chromatography. The liquid chromatographic analysis can be conducted, for example, under the following conditions.

Column Inertsil

ODS-3 250 mm×4.6 mm I.D., 5.0 μm (product of GL Science), detector L-7490 R1 detector (product of Hitachi Ltd.), mobile phase [$Na_2HPO_4$ 1 mM+$KH_2PO_4$ 9 mM+$NaClO_4$ 100 mM]/$H_2O$, flow rate 1.0 ml/min., column temp. 40° C.

BEST MODE OF CARRYING OUT THE INVENTION

The present invention will be described with reference to the following Examples, but is not limited to these examples.

EXAMPLE 1

Calcium oxide (1.0 g) was added to 100 g of an electrolytic solution of the following composition within a glove box having an argon atmosphere with a dew point of −60° C.

N-Methoxymethyl-N-methylpyrrolidinium tetrafluoroborate 30 wt. %

Propylene carbonate 70 wt. %

$H_2O$ 30 ppm

Methylpyrrolidine tetrafluoroborate 300 ppm

The mixture was stirred at 40° C. for 1 hour and thereafter filtered with a membrane filter to remove the resulting calcium tetrafluoroborate and calcium hydroxide and an excess of calcium oxide. The filtrate was held in a vacuum of 1 mmHg at 25° C. for 1 hour to remove methylpyrrolidine and water. The resulting mixture was returned to atmospheric pressure in argon gas having a dew point of −60° C. and analyzed.

N-Methoxymethyl-N-methylpyrrolidinium tetrafluoroborate 30 wt. %

Propylene carbonate 70 wt. %

$H_2O$ 9 ppm

Methylpyrrolidine tetrafluoroborate detection limit (10 ppm>)

EXAMPLE 2

Magnesium oxide (1.0 g) was added to 100 g of an electrolytic solution of the following composition within a glove box having an argon atmosphere with a dew point of −60° C.

N-Methoxymethyl-N,N,N-trimethylammonium tetrafluoroborate 30 wt. %

Propylene carbonate 70 wt. %

H2O 30 ppm

N,N,N-Trimethylammonium tetrafluoroborate 300 ppm

The mixture was stirred at 80° C. for 1 hour and thereafter filtered with a membrane filter. The filtrate was held in a vacuum of 1 mmHg at 25° C. for 1 hour. The resulting mixture was returned to atmospheric pressure in argon gas having a dew point of −60° C. and analyzed.

N-Methoxymethyl-N,N,N-trimethylammonium tetrafluoroborate 30 wt. %

Propylene carbonate 70 wt. %

H2O 12 ppm

N-Methoxymethyl-N,N,N-trimethylammonium tetrafluoroborate 30 ppm

EXAMPLE 3

Barium oxide (1.0 g) was added to 100 g of an electrolytic solution of the following composition within a glove box having an argon atmosphere with a dew point of −60° C.

N-Methoxymethyl-N-methylpyrrolidinium tetrafluoroborate 30 wt. %

Propylene carbonate 70 wt. %

H2O 30 ppm

Methylpyrrolidine tetrafluoroborate 300 ppm

The mixture was stirred at 40° C. for 1 hour and thereafter filtered with a membrane filter. The filtrate was held in a vacuum of 1 mmHg at 25° C. for 1 hour. The resulting mixture was returned to atmospheric pressure in argon gas having a dew point of −60° C. and analyzed.

N-Methoxymethyl-N-methylpyrrolidinium tetrafluoroborate 30 wt. %

Propylene carbonate 70 wt. %

H2O 7 ppm

Methylpyrrolidine tetrafluoroborate detection limit (10 ppm>)

EXAMPLE 4

Zinc oxide (1.0 g) was added to 100 g of an electrolytic solution of the following composition within a glove box having an argon atmosphere with a dew point of −60° C.

N-Ethyl-N-methylimidazolium tetrafluoroborate 30 wt. %

Propylene carbonate 70 wt. %

H2O 30 ppm

Ethylimidazole tetrafluoroborate 300 ppm

The mixture was stirred at 60° C. for 1 hour and thereafter filtered with a membrane filter. The filtrate was held in a vacuum of 1 mmHg at 25° C. for 1 hour. The resulting mixture was returned to atmospheric pressure in argon gas having a dew point of −60° C. and analyzed.

N-Ethyl-N-methylimidazolium tetrafluoroborate 30 wt. %

Propylene carbonate 70 wt. %

H2O 9 ppm

Ethylimidazole tetrafluoroborate detection limit (10 ppm>)

EXAMPLE 5

Aluminum oxide (1.0 g) was added to 100 g of an electrolytic solution of the following composition within a glove box having an argon atmosphere with a dew point of −60° C.

N-Methoxymethyl-N-methylpyrrolidinium tetrafluoroborate 30 wt. %

Propylene carbonate 70 wt. %

H2O 30 ppm

Methylpyrrolidine tetrafluoroborate 300 ppm

The mixture was stirred at 80° C. for 1 hour and thereafter filtered with a membrane filter. The filtrate was held in a vacuum of 1 mmHg at 25° C. for 1 hour. The resulting mixture was returned to atmospheric pressure in argon gas having a dew point of −60° C. and analyzed.

N-Methoxymethyl-N-methylpyrrolidinium tetrafluoroborate 30 wt. %

Propylene carbonate 70 wt. %

H2O 15 ppm

Methylpyrrolidine tetrafluoroborate 50 ppm

EXAMPLE 6

A 30.0 g quantity of N-methylpyrrolidine (reagent, product of Tokyo Kasei Co., Ltd.) was dissolved in 120 g of methyl acetate, followed by replacement with nitrogen. A 31.2 g quantity of chloromethyl methyl ether (reagent, product of Tokyo Kasei Co., Ltd.) was added dropwise to the solution at 5° C. over a period of 1 hour. The mixture was stirred at 5° C. for 1 hour, the temperature was slowly raised, and the mixture was stirred at room temperature for 10 hours to complete the reaction. The reaction mixture was filtered, and the solid product was washed with 150 g of methyl acetate and 150 g of acetone. The washed product was dried in a vacuum, giving 53.7 g of N-methoxymethyl-N-methylpyrrolidinium chloride. The chloride salt (53.7 g) obtained was dissolved in 125 g of methanol, and 99.6 g of 30% $HBF_4$ methanol solution was added to the solution. Nitrogen was bubbled through the mixture at 130° C. to remove methanol, hydrogen chloride and excessive $HBF_4$ to obtain 70.2 g of the desired electrolyte, i.e., N-methoxymethyl-N-methylpyrrolidinium tetrafluoroborate (water content: 20 ppm). The electrolyte was used to prepare 100 g of an electrolytic solution of the following composition within a glove box having an argon atmosphere with a dew point of −60° C. Calcium oxide (1.0 g) was thereafter added to the solution.

N-Methoxymethyl-N-methylpyrrolidinium tetrafluoroborate 30 wt. %

Propylene carbonate 70 wt. %

H2O 18 ppm

Methylpyrrolidine tetrafluoroborate 400 ppm

The mixture was stirred at 40° C. for 1 hour and then filtered with a membrane filter. The filtrate was held in a vacuum of 1 mmHg at 25° C. for 1 hour. The resulting mixture was returned to atmospheric pressure in argon gas having a dew point of −60° C. and analyzed.

N-Methoxymethyl-N-methylpyrrolidinium tetrafluoroborate 30 wt. %

Propylene carbonate 70 wt. %

H2O 8 ppm

Methylpyrrolidine tetrafluoroborate detection limit (10 ppm>)

EXAMPLE 7

Calcium hydroxide (1.0 g) was added to 100 g of an electrolytic solution of the following composition within a glove box having an argon atmosphere with a dew point of −60° C.

N-Methoxymethyl-N-methylpyrrolidinium tetrafluoroborate 30 wt. %

Propylene carbonate 70 wt. %

H2O 20 ppm

Methylpyrrolidine tetrafluoroborate 300 ppm

The mixture was stirred at 40° C. for 1 hour and thereafter filtered with a membrane filter. The filtrate was held in a vacuum of 1 mmHg at 25° C. for 1 hour. The resulting mixture was returned to atmospheric pressure in argon gas having a dew point of −60° C. and analyzed.

N-Methoxymethyl-N-methylpyrrolidinium tetrafluoroborate 30 wt. %

Propylene carbonate 70 wt. %

H2O 12 ppm

Methylpyrrolidine tetrafluoroborate detection limit (10 ppm>)

EXAMPLE 8

Aluminum hydroxide (1.0 g) was added to 100 g of an electrolytic solution of the following composition within a glove box having an argon atmosphere with a dew point of −60° C.

N-Methoxymethyl-N-methylpyrrolidinium tetrafluoroborate 30 wt. %

Propylene carbonate 70 wt. %

H2O 20 ppm

Methylpyrrolidine tetrafluoroborate 300 ppm

The mixture was stirred at 40° C. for 1 hour and thereafter filtered with a membrane filter. The filtrate was held in a vacuum of 1 mmHg at 25° C. for 1 hour. The resulting mixture was returned to atmospheric pressure in argon gas having a dew point of −60° C. and analyzed.

N-Methoxymethyl-N-methylpyrrolidinium tetrafluoroborate 30 wt. %

Propylene carbonate 70 wt. %

H2O 12 ppm

Methylpyrrolidine tetrafluoroborate detection limit (10 ppm>)

EXAMPLE 9

An electrolytic solution of the following composition was obtained in the same manner as in Example 8 except of using 1.0 g of barium oxide and 1.0 g of barium hydroxide in place of 1.0 g of aluminum hydroxide.

N-Methoxymethyl-N-methylpyrrolidinium tetrafluoroborate 30 wt. %

Propylene carbonate 70 wt. %

H2O 10 ppm

Methylpyrrolidine tetrafluoroborate detection limit (10 ppm>)

F ion 1 ppm

EXAMPLE 10

An electrolytic solution of the following composition was obtained in the same manner as in Example 8 except of using 1.0 g of barium oxide and 1.0 g of magnesium hydroxide in place of 1.0 g of aluminum hydroxide.

N-Methoxymethyl-N-methylpyrrolidinium tetrafluoroborate 30 wt. %

Propylene carbonate 70 wt. %

H2O 10 ppm

Methylpyrrolidine tetrafluoroborate detection limit (10 ppm>)

F ion 1 ppm

EXAMPLE 11

An electrolytic solution of the following composition was obtained in the same manner as in Example 8 except of using 1.0 g of calcium oxide and 1.0 g of calcium hydroxide in place of 1.0 g of aluminum hydroxide.

N-Methoxymethyl-N-methylpyrrolidinium tetrafluoroborate 30 wt. %

Propylene carbonate 70 wt. %

H2O 10 ppm

Methylpyrrolidine tetrafluoroborate detection limit (10 ppm>)

F ion 1 ppm

EXAMPLE 12

An electrolytic solution of the following composition was obtained in the same manner as in Example 8 except of using 1.0 g of calcium oxide and 1.0 g of aluminum hydroxide in place of 1.0 g of aluminum hydroxide.

N-Methoxymethyl-N-methylpyrrolidinium tetrafluoroborate 30 wt. %

Propylene carbonate 70 wt. %

H2O 10 ppm

Methylpyrrolidine tetrafluoroborate detection limit (10 ppm>)

F ion 1 ppm

EXAMPLE 13

An electrolytic solution of the following composition was obtained in the same manner as in Example 8 except of using 1.0 g of magnesium oxide and 1.0 g of barium hydroxide in place of 1.0 g of aluminum hydroxide.

N-Methoxymethyl-N-methylpyrrolidinium tetrafluoroborate 30 wt. %

Propylene carbonate 70 wt. %

H2O 10 ppm

Methylpyrrolidine tetrafluoroborate detection limit (10 ppm>)

F ion 1 ppm

EXAMPLE 14

A 30.0 g quantity of N-methylpyrrolidine (reagent, product of Tokyo Kasei Co., Ltd.) was dissolved in 120 g of methyl acetate, followed by replacement with nitrogen. A 31.2 g quantity of chloromethyl methyl ether (reagent, product of Tokyo Kasei Co., Ltd.) was added dropwise to the solution at 5° C. over a period of 1 hour. The mixture was stirred at 5° C. for 1 hour, the temperature was slowly raised, and the mixture was stirred at room temperature for 10 hours to complete the reaction. The reaction mixture was filtered, and the solid product was washed with 150 g of methyl acetate and 150 g of acetone. The washed product was dried in a vacuum, giving 53.7 g of N-methoxymethyl-N-methylpyrrolidinium chloride. To the chloride salt (53.7 g) obtained was added 71.2 g of 42% aqueous solution of $HBF_4$ to dissolve the salt. Nitrogen was bubbled through the solution at 130° C. to remove water, hydrogen chloride and excessive $HBF_4$. To the solution was added 70 ml of methanol, and nitrogen was bubbled through the mixture at 130° C. to further remove water, hydrogen chloride and excessive $HBF_4$ and obtain 68.2 g of the desired electrolyte, i.e., N-methoxymethyl-N-methylpyrrolidinium tetrafluoroborate (water: 30 ppm, methylpyrrolidine tetrafluoroborate: 4000 ppm).

To 68.2 g of the electrolyte were added 2.0 g of barium chloride and 70 ml of methanol within a glove box having an argon atmosphere with a dew point of −60° C. Nitrogen was bubbled through the mixture at 130° C. to remove the methanol, followed by filtration with a membrane filter and analysis.

N-Methoxymethyl-N-methylpyrrolidinium tetrafluoroborate 100 wt. % (containing the following impurities in amounts of ppm level)

$H_2O$ 10 ppm

Methylpyrrolidine tetrafluoroborate detection limit (10 ppm>)

EXAMPLE 15

An electrolytic solution of the following composition was obtained in the same manner as in Example 14 except of using 2.0 g of calcium oxide in place of 2.0 g of barium oxide.

N-Methoxymethyl-N-methylpyrrolidinium tetrafluoroborate 100 wt. % (containing the following impurities in amounts of ppm level)

$H_2O$ 10 ppm

Methylpyrrolidine tetrafluoroborate detection limit (10 ppm>)

EXAMPLE 16

An electrolytic solution of the following composition was obtained in the same manner as in Example 14 except of using 2.0 g of calcium hydroxide in place of 2.0 g of barium oxide.

N-Methoxymethyl-N-methylpyrrolidinium tetrafluoroborate 100 wt. % (containing the following impurities in amounts of ppm level)

$H_2O$ 10 ppm

Methylpyrrolidine tetrafluoroborate detection limit (10 ppm>)

EXAMPLE 17

An electrolytic solution of the following composition was obtained in the same manner as in Example 14 except of using 2.0 g of barium oxide and 2.0 g of barium hydroxide in place of 2.0 g of barium oxide.

N-Methoxymethyl-N-methylpyrrolidinium tetrafluoroborate 100 wt. % (containing the following impurities in amounts of ppm level)

$H_2O$ 10 ppm

Methylpyrrolidine tetrafluoroborate detection limit (10 ppm>)

F ion 1 ppm

EXAMPLE 18

An electrolytic solution of the following composition was obtained in the same manner as in Example 14 except of using 2.0 g of barium oxide and 2.0 g of magnesium hydroxide in place of 2.0 g of barium oxide.

N-Methoxymethyl-N-methylpyrrolidinium tetrafluoroborate 100 wt. % (containing the following impurities in amounts of ppm level)

$H_2O$ 10 ppm

Methylpyrrolidine tetrafluoroborate detection limit (10 ppm>)

F ion 1 ppm

EXAMPLE 19

An electrolytic solution of the following composition was obtained in the same manner as in Example 14 except of using 2.0 g of calcium oxide and 2.0 g of calcium hydroxide in place of 2.0 g of barium oxide.

N-Methoxymethyl-N-methylpyrrolidinium tetrafluoroborate 100 wt. % (containing the following impurities in amounts of ppm level)

$H_2O$ 10 ppm

Methylpyrrolidine tetrafluoroborate detection limit (10 ppm>)

F ion 1 ppm

EXAMPLE 20

An electrolytic solution of the following composition was obtained in the same manner as in Example 14 except of using 2.0 g of calcium oxide and 2.0 g of aluminum hydroxide in place of 2.0 g of barium oxide.

N-Methoxymethyl-N-methylpyrrolidinium tetrafluoroborate 100 wt. % (containing the following impurities in amounts of ppm level)

$H_2O$ 10 ppm

Methylpyrrolidine tetrafluoroborate detection limit (10 ppm>)

F ion 1 ppm

EXAMPLE 21

An electrolytic solution of the following composition was obtained in the same manner as in Example 14 except of using 2.0 g of magnesium oxide and 2.0 g of barium hydroxide in place of 2.0 g of barium oxide.

N-Methoxymethyl-N-methylpyrrolidinium tetrafluoroborate 100 wt. % (containing the following impurities in amounts of ppm level)

$H_2O$ 10 ppm

Methylpyrrolidine tetrafluoroborate detection limit (10 ppm>)

F ion 1 ppm

EXAMPLE 22

Barium oxide (2.0 g) was added to 70 g of an electrolytic solution of the following composition within a glove box having an argon atmosphere with a dew point of −60° C.

N-Methyl-N-ethylimidazolium tetrafluoroborate 100 wt. % (containing the following impurities in amounts of ppm level)

$H_2O$ 30 ppm

Ethylimidazole tetrafluoroborate 300 ppm

To the mixture was added 70 ml of methanol and then nitrogen was bubbled at 130° C. to remove methanol. The resulting mixture was filtered with a membrane filter and analyzed.

N-Methyl-N-ethylimidazolium tetrafluoroborate 100 wt. % (containing the following impurities in amounts of ppm level)

$H_2O$ 10 ppm

Ethylimidazole tetrafluoroborate detection limit (10 ppm>)

EXAMPLE 23

An electrolytic solution of the following composition was obtained in the same manner as in Example 22 except of using 2.0 g of barium oxide and 2.0 g of barium hydroxide in place of 2.0 g of barium oxide.

N-Methyl-N-ethylimidazolium tetrafluoroborate 100 wt. % (containing the following impurities in amounts of ppm level)

$H_2O$ 10 ppm

Ethylimidazole tetrafluoroborate detection limit (10 ppm>)

F ion 1 ppm

INDUSTRIAL APPLICABILITY

According to the invention, the amounts of a tertiary amine and tertiary amine protonic acid salt contained as impurities in quaternary ammonium salts can be reduced.

The quaternary ammonium salt reduced in impurity contents is favorably usable as an electrolyte in electric double layer capacitors, electrolytic capacitors and like capacitor elements.

The electric double layer capacitor and electrolytic capacitor incorporating this electrolyte are improved in voltage resistance and long-term reliability.

The invention claimed is:

1. A process for preparing a high-purity quaternary ammonium salt comprising:

(1) adding an oxide or hydroxide of a Group 1, 2, 12 or 13 metal to a quaternary ammonium salt containing a protonic acid salt of a tertiary amine as an impurity and thereby neutralizing the tertiary amine protonic acid salt with the metal oxide or hydroxide to convert the acid salt to a tertiary amine and water and to convert the metal oxide or hydroxide to a metal salt at the same time, and (2) removing the tertiary amine, water and metal salt produced from the system.

2. A process for preparing a high-purity quaternary ammonium salt comprising:

(1) reacting a tertiary amine with an alkyl halide having or not having a substituent to obtain a quaternary ammonium halide salt, (2) reacting an acid compound with the halide salt to obtain a quaternary ammonium salt containing a tertiary amine protonic acid salt as an impurity, (3) adding an oxide or hydroxide of a Group 1, 2, 12 or 13 metal to the quaternary ammonium salt and thereby neutralizing the tertiary amine protonic acid salt with the metal oxide or hydroxide to convert the acid salt to a tertiary amine and water and to convert the metal oxide or hydroxide to a metal salt at the same time, and (4) removing the tertiary amine, water and metal salt produced from the system.

3. A process as defined in claim 2 wherein the acid compound is $CF_3CO_2H$, $CF_3SO_3H$, $HBF_4$, $HAlF_4$, $HClBF_3$ or $(FSO_2)_2NH$.

4. A process as defined in claim 1 wherein the metal oxide or metal hydroxide is CaO, MgO, BaO, ZnO, $Al_2O_3$, $Ca(OH)_2$, $Mg(OH)_2$, $Ba(OH)_2$, $Zn(OH)_2$, $Al(OH)_3$ or LiOH.

5. A process as defined in claim 4 wherein the metal oxide or metal hydroxide is CaO, MgO, BaO, ZnO, $Al_2O_3$, $Ca(OH)_2$, $Mg(OH)_2$, $Ba(OH)_2$ or $Al(OH)_3$.

6. A process as defined in claim 2 wherein the metal oxide or metal hydroxide is CaO, MgO, BaO, ZnO, $Al_2O_3$, $Ca(OH)_2$, $Mg(OH)_2$, $Ba(OH)_2$, $Zn(OH)_2$, $Al(OH)_3$ or LiOH.

7. A process as defined in claim 6 wherein the metal oxide or metal hydroxide is CaO, MgO, BaO, ZnO, $Al_2O_3$, $Ca(OH)_2$, $Mg(OH)_2$, $Ba(OH)_2$ or $Al(OH)_3$.

* * * * *